United States Patent [19]

Liedtke

[11] Patent Number: 5,776,952

[45] Date of Patent: Jul. 7, 1998

[54] METHOD AND COMPOSITION FOR TOPICAL THERAPY OF BACK PAIN AND MUSCLE TENSION

[75] Inventor: Rainer K. Liedtke, Munich, Germany

[73] Assignee: American Pharmed Labs, Inc., New York, N.Y.

[21] Appl. No.: 682,352

[22] Filed: Jul. 17, 1996

[30] Foreign Application Priority Data

Jul. 17, 1995 [DE] Germany .................. 195 26 031.7

[51] Int. Cl.⁶ .................. A61K 31/445; A61K 31/24; A61K 31/16; A61K 31/135

[52] U.S. Cl. .................. 514/330; 514/535; 514/626; 514/646; 514/817; 514/818; 514/906

[58] Field of Search .................. 514/330, 535, 514/626, 817, 818, 906, 646

[56] References Cited

PUBLICATIONS

CA 113:178256, Gale et al., 1989.

*Primary Examiner*—Kimberly Jordan
*Attorney, Agent, or Firm*—Oblon, Spivak, McClelland, Maier & Neustadt, P.C.

[57] ABSTRACT

A composition for topical therapy for symptoms of back pain, muscle tension or myofascial pain or a combination thereof, which comprises a topical carrier system for intact skin of the back or outer synovial membranes or both, which comprises a therapeutic dose of a local anesthetic, and which applies the local anesthetic to a region of skin lying beneath the topical carrier system.

10 Claims, No Drawings

METHOD AND COMPOSITION FOR TOPICAL THERAPY OF BACK PAIN AND MUSCLE TENSION

BACKGROUND OF THE INVENTION

1. Field of the Invention

The present invention relates to a method and composition for topical therapy of back pain and muscle tension.

2. Description of the Background

It is known that back pain, muscle tension, and myofascial pain predominantly have neurological and muscular causes, however, psychosomatic stress factors, physical environmental factors, nonfunctional, active or passive fixation in body posture, deficient movement, functional or organic dysfunction of the spinal column due to stress, for example, intervertebral disk damage, are also implicated.

Approximately 80% of the population with varying frequency, experiences back pain. Back pain is also one of the most important causes of lost work time with all of the attendant economic results. Presently, the symptoms of back pain are predominantly treated pharmacologically with systemically active, nonopiate, oral or injectable analgesics and antiphlogistics, and, in part, in combination with psychosomatic or physical therapy, sometimes also in combination with other methods, such as, acupuncture. The last resort for diseases of the intervertebral disk is surgery.

These pharmacotherapies, however, still do not represent sufficiently tolerable and effective forms of treatment. Presently, derivatives of salicylic acid, preferably, acetylsalicylic acid, nonsteroidal antiphlogistics, for example, ibuprofen, or aniline derivatives, for example, paracetamol, are used as the pharmacological principles (e.g., K. Brune, W. Beck in: M. Zenz, I. Jura (Editors) Lehrbuch der Scherztherapie (Manual of Pain Therapy), WFG, Stuttgart, 1993, pp. 121–135). Furthermore, central or peripheral muscle relaxants are used, as well as tranquilizers of the benzodiazepine group or different antidepressants.

Unfortunately, all systemic analgesic and also muscle-relaxant therapies have a considerable number of undesirable side effects in common. The salicylic acid derivatives and nonsteroidal antiphlogistics are associated considerably and frequently with gastric disorders as a result of the antiproliferative active mechanism. Paracetamol, with a weaker effect, is associated with metabolic stress of liver and kidney functions, especially when used for a prolonged period of time and at required higher doses. Muscle relaxants are associated in particular with a high rate of sedation and gastrointestinal disorders. Therefore, application of these therapies is limited by the spectrum of undesirable, product-specific effects in each case, because systemic interventions involve all of the organs and the organ systems.

A more effective pharmacological principle might be a suitable form of low-dosed local anesthetics. Amide and ester group-containing local anesthetics, for example, lidocaine of the amide type, exhibit, as a pharmacological active mechanism, an inhibition of the rapid sodium ion influx in nerve fibers. In this manner, the impulse conduction of the nerve path is blocked, which in principle involves all regional nerve fibers. The sensory, anatomically thinner fibers are more sensitive than the motoric fibers due to their morphology (G. R. Strichartz (Editor) Local Anesthetics, Handbook of Experimental Pharmacology, Vol. 81, Springer, Berlin-N.Y., 1987). The active effects can also be differentiated in this way.

Systemic application of local anesthetics might be applied invasively by means of injection. However, this option is practically eliminated due to the danger of systemic overdosage with, among others, serious cardiac side effects. Direct application of local anesthetics through local injection is technically possible and is performed in different ways. However, local injections are not only painful, but can also never be done directly by the patient. The local surface injection technique involves so-called neural therapy with muscular trigger points and requires experienced medical handling and technique (J. T. Travell, D. G. Simons, Myofascial Pain and Dysfunction, Vol. I/II, Williams & Wilkins, Baltimore, 1983). Therefore, this option is limited to use in clinically severe disorders. Further, use of conventional topical formulations, for example, creams, allows neither exact dosage nor continuous penetration over a prolonged period of application.

SUMMARY OF THE INVENTION

Accordingly, it is an object of the present invention to provide an improved method of therapy for back pain, muscle tension and myofascial pain.

It is also an object of the present invention to provide a composition for the treatment of back pain, muscle pain and myofascial pain.

The above objects and others are provided by a composition for topical therapy of symptoms of back pain, muscle tension and myofascial pain, which contains a topical carrier system for intact mammalian skin of the back or outer synovial membrane, which contains a therapeutically effective amount or dose of a local anesthetic, whereby the local anesthetic is applied to a region of skin lying beneath the topical carrier system.

DETAILED DESCRIPTION OF THE PREFERRED EMBODIMENTS

The present invention provides a topical carrier system, suitable for intact skin of the back or outer synovial membranes of a mammal, which is charged with a therapeutic dose of a local anesthetic, whereby the local anesthetic is applied specifically to the skin region located underneath the topical carrier system.

Generally, the present invention may be used in conjunction with any mammal, such as horses, cows, dogs or cats, however, it is particularly advantageous when used with humans.

To improve efficacy and tolerability of the topical therapy, in a further embodiment of the invention, local anesthetics which are amide group- or ester groupcontaining are contained, especially lidocaine, tetracaine, bupivacaine, prilocaine, mepivacaine, etidocaine, as well as procaine and benzocaine, and these substances are present in concentration ranges of about 0.5–40% by weight based upon the total weight of the composition.

However, any amide group- and/or ester group-containing local anesthetic may be used either alone or in combination with others. Other such local anesthetics are, for example, the esters propoxycaine, hydroxyprocaine, chloroprocaine, ambucaine, metabutoxycaine, proparacaine, paraethoxycaine, butacaine, isobucaine, hexylcaine, piridocaine, piperocaine and cyclomethycaine; or the amides procainamide, dibucaine, pyrrocaine and tolycaine. All of these compounds are known with synthetic methodologies for preparing the same being described in *Organic Chemistry of Drug Synthesis*, Lednicer et al (Wiley, 1977).

To improve efficacy and tolerability of the therapy, in another embodiment of the invention, two or more local anesthetics with different pharmacokinetics are combined in the topical carrier system used, and these individual substances are present in such concentrations that the total concentration of the two or more active ingredients is not more than 40% by weight based on the total weight of the composition.

Further, to make the therapy as a whole, safer and more manageable, in a further embodiment of the invention, the topical carrier system is presented in a form which corresponds to the specific application field of back skin or outer synovial membranes. Thus, the external shape of the topical carrier system is round, oval, or rectangular, with concave or convex recesses, or the carrier system can be segmented by the user into appropriate shapes, with or without additional aids.

Quite surprisingly, no therapy of back pain, muscle tension, and myofascial pain, using a carrier system with local anesthetics applied to so-called trigger points, has ever before been described. One advantage which is now achieved by virtue of the present invention is that with this new principle, a noninvasive and local treatment option for symptoms of back pain, muscle tension, and myofascial pain is available for the first time.

The present topical therapy with local anesthetics in a topical carrier system also makes possible a locally targeted and long-term therapeutically effective treatment of the terminal and functionally interlinked nerve paths in the area of the surface skin.

Since this surface area also has good cutaneous absorption capacity, lower topical doses can also be used. Advantageously, systemic danger, as it exists with customary oral or injectable analgesics, antiphlogistics, or muscle relaxants, is avoided, because the local anesthetics, for example, lidocaine, are metabolized to a large extent with delayed cutaneous absorption, so that no systemic activity levels appear with the corresponding organ stresses.

Generally, although conventional dosages of local anesthetics may be used, it is preferred that the therapeutically effective topical amount of local anesthetic in the carrier is, for lidocaine, for example, in the range of about 10 mg to 50 mg for delivery to the intact skin over a span of about 12 to 36 hours at a rate in the range of about 0.05 to 1 mg/cm$^2$ per hour. However, other dosage amounts may be used depending upon the particular local anesthetics used.

The present method and composition are also advantageous in that the therapy can be controlled and maintained with low doses and, as needed, can be interrupted by removal of the carrier.

Hence, the present topical therapy of back pain, muscle tension, and myofascial pain avoids the conventional undesirable side effects such as those exhibited by systemic therapies with, among others, analgesics, antiphlogistics, or muscle relaxants, since the prior distribution of the active ingredient through the entire body which stresses the other organs and organ systems is avoided. In addition, local anesthetics also exhibit good local tissue tolerability.

As examples of technically suitable designs of topical carrier system which may be used with local anesthetics, in accordance with the present invention, for the therapy of symptoms of back pain, muscle tension, and myofascial pain, the technical carrier systems in U.S. Pat. No. 4,765,986, DE P3716575.45, and DE P3811564.45 are noted, without limiting the present invention to these described techniques. U.S. Pat. No. 4,765,986 is incorporated herein in the entirety by reference.

Having described the present invention, it will be apparent to one of ordinary skill in the art that many changes and modifications can be made to the above-described embodiments without departing from the spirit and scope of the present invention.

What is claimed as new and desired to be secured by Letters Patent of the United States is:

1. A method for topical therapy for symptoms of back pain, muscle tension or myofascial pain or a combination thereof, which comprises administering to a mammal in need thereof a topical carrier system for intact mammalian skin of the back or outer synovial membranes or both, which topical carrier system comprises an analgesically effective dose of a local anesthetic, whereby the local anesthetic is administered to a region of skin lying beneath the topical carrier system.

2. The method according to claim 1, wherein the local anesthetic is an amide or an ester group-containing local anesthetic.

3. The method according to claim 1, wherein the local anesthetic is selected from the group consisting of lidocaine, tetracaine, prilocaine, bupivacaine, mepivacaine, etidocaine, procaine, benzocaine propoxycaine, hydroxyprocaine, chloroprocaine, ambucaine, metabutoxycaine, proparacaine, paraethoxycaine, butacaine, isobucaine, hexylcaine, piridocaine, piperocaine, cyclomethycaine, procainamide, dibucaine, pyrrocaine and tolycaine.

4. The method according to clam 1, which comprises administering two or more local anesthetics from said topical carrier system, each having different pharmacokinetics from the other or others.

5. The method according to claim 1, which comprises administering about 0.5–40% by weight of said local anesthetic based upon the weight of the composition.

6. The method according to claim 1, wherein the local anesthetic is lidocaine.

7. The method according to claim 6, wherein the analgesically effective dose is about 10 mg to 50 mg.

8. The method according to claim 1, wherein said topical carrier system has a shape which is round, oval or rectangular.

9. The method according to claim 1, which has concave or convex recesses.

10. The method according to claim 1, which is segmented.

\* \* \* \* \*